(12) United States Patent
Drew

(10) Patent No.: US 8,250,752 B2
(45) Date of Patent: Aug. 28, 2012

(54) METHOD OF ASSEMBLING A CONNECTOR ASSEMBLY FOR A MEDICAL DEVICE

(75) Inventor: Michael H. Z. Drew, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 868 days.

(21) Appl. No.: 12/370,686

(22) Filed: Feb. 13, 2009

(65) Prior Publication Data

US 2009/0144973 A1 Jun. 11, 2009

Related U.S. Application Data

(63) Continuation of application No. 11/697,386, filed on Apr. 6, 2007, now Pat. No. 7,510,447.

(51) Int. Cl.
*H01R 43/00* (2006.01)
(52) U.S. Cl. ............... 29/857; 29/874; 29/876; 439/669
(58) Field of Classification Search ................... 29/857, 29/874, 876; 439/669
See application file for complete search history.

(56) References Cited

U.S. PATENT DOCUMENTS

| | | | |
|---|---|---|---|
| 4,445,511 A | 5/1984 | Cowdery et al. | |
| 4,715,380 A | 12/1987 | Harris | |
| 5,275,620 A | 1/1994 | Darby et al. | |
| 5,769,671 A | 6/1998 | Lim | |
| 6,725,096 B2 | 4/2004 | Chinn et al. | |
| 6,741,892 B1 | 5/2004 | Meadows et al. | |
| 6,895,276 B2 | 5/2005 | Kast et al. | |
| 7,130,699 B2 | 10/2006 | Huff et al. | |
| 7,402,083 B2 | 7/2008 | Kast et al. | |
| 7,510,447 B2* | 3/2009 | Drew | 439/669 |
| 2004/0064164 A1* | 4/2004 | Ries et al. | 607/37 |
| 2005/0027325 A1 | 2/2005 | Lahti et al. | |
| 2005/0027326 A1 | 2/2005 | Ries et al. | |
| 2005/0027327 A1 | 2/2005 | Ries et al. | |

\* cited by examiner

*Primary Examiner* — Carl Arbes

(57) ABSTRACT

A connector assembly for a medical device includes at least one contact assembly, and each of the at least one contact assembly includes a mounting member, a first contact clip and a second contact clip. A method for assembling the connector assembly includes mounting the first contact clip to one of a first pair of opposing mounting sidewalls, on a first side of a shoulder of the mounting member, and mounting a second contact clip to one of a second pair of opposing mounting sidewalls of the mounting member, on a second side of the shoulder. The mounting member includes a bore, to receive axial insertion of a medical electrical lead connector therein, and the first and second pairs of opposing mounting sidewalls extend about the bore, such that opposing curved legs of each of the mounted connector clips bend into and out from the bore.

13 Claims, 7 Drawing Sheets ent application is a continuation application of
METHOD OF ASSEMBLING A CONNECTOR ASSEMBLY FOR A MEDICAL DEVICE The present application is a continuation application of U.S. application Ser. No. 11/697,386, filed Apr. 6, 2007, now allowed, which is hereby incorporated by reference, in its entirety.

TECHNICAL FIELD

The present invention pertains to medical device and more particularly to medical device connector assemblies and contact assemblies thereof.

BACKGROUND

A host of medical devices include electrical connector assemblies for coupling with a type of medical electrical lead connector that is formed along a proximal portion of the lead and includes a plurality of connector elements disposed along a length thereof. These connector assemblies typically include a plurality of electrical contacts positioned within a bore of what is typically called a device connector module, or header, at locations corresponding to the connector elements of the lead connector, in order to mate with the corresponding connector elements when the connector is fully inserted within the bore. Some device connector assemblies further include sealing elements located between the electrical contacts to mate with insulative spacers located between the connector elements of the lead connector, and thereby provide electrical isolation between each mating contact and connector element. Although a variety of contact assemblies for such connector assemblies are known in the art, there is still a need for new contact assembly designs that provide for stable electrical connection without increasing a bulk, complexity or cost of the connector assemblies.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
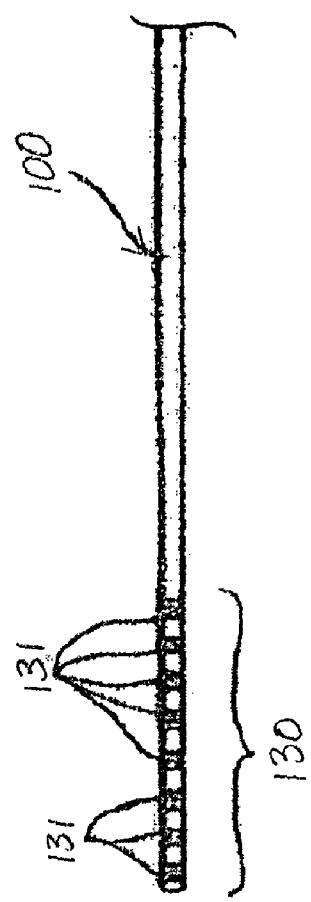
FIG. 1A is perspective view of a portion of an exemplary medical system that may include embodiments of the present invention.
Figure 1A:
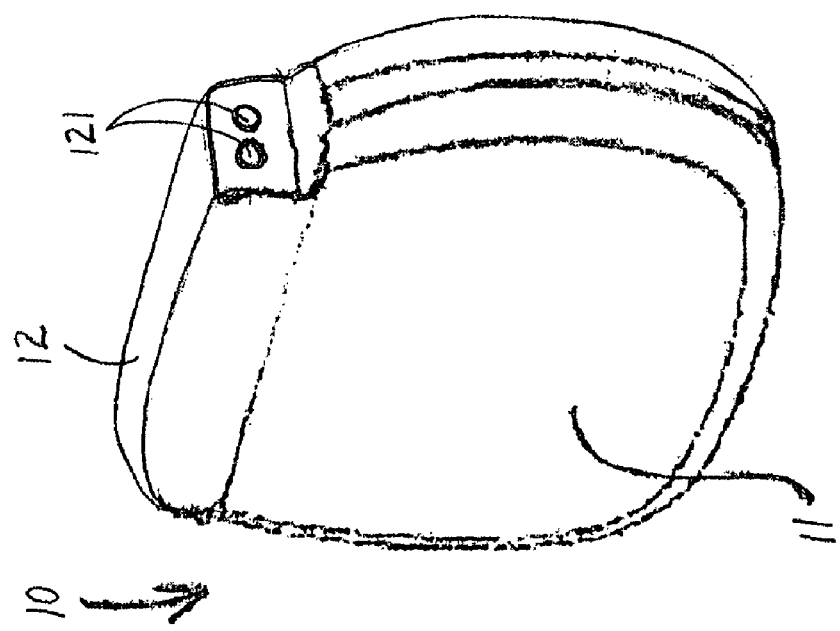

FIG. 1A is perspective view of a portion of an exemplary medical system that may include embodiments of the present invention. FIG. 1A illustrates the medical system including a medical device 10 and a medical electrical lead 100; a connector 130 of lead 100 is shown terminating a proximal end thereof and including a plurality of connector elements 131 spaced apart along a length of connector 130 by a plurality of interposed insulative spacers. Materials, components and construction methods for lead connectors, such as connector 130, are well known to those skilled in the art. FIG. 1A further illustrates device 10 including a housing 11 and a connector module 12 mounted thereto; module 12 includes a pair of bores 121 formed by connector assemblies 120, which are contained within module 12 and are shown in FIG. 1B.

Figure 1B:
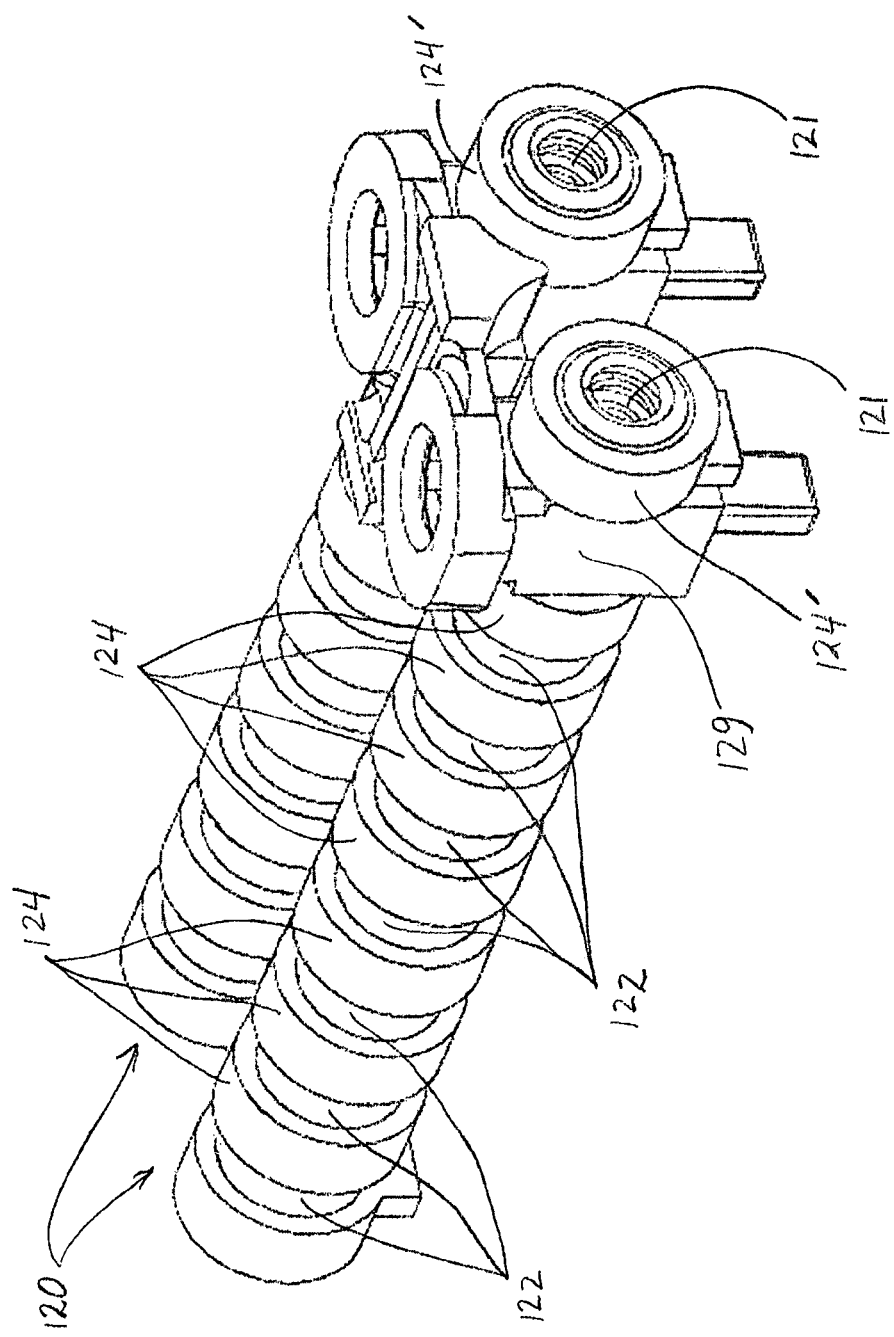
FIG. 1B is a perspective view of a pair of connector assemblies from the system show in FIG. 1A, according to an exemplary embodiment of the present invention.

FIG. 1B is a perspective view of connector assemblies 120, according to an exemplary embodiment of the present invention. FIG. 1B illustrates each connector assembly 120 including a plurality of contact assemblies 122, 129 spaced apart from one another, by a plurality of seal members 124, along a length of bore 121. According to the illustrated embodiment, contact assembly 129 is a set screw-type contact known to those skilled in the art. A location of each contact assembly 122, 129 corresponds to a location of each connector element 131 of lead connector 130 to provide electrical coupling between the corresponding connector element 131 and circuitry contained within housing 11, when connector 130 is fully inserted into either of bores 121; and interspersed seal members 124 provide electrical isolation between the couplings. An additional sealing member 124' is shown located at an entry to each bore; sealing members 124' may prevent an ingress of bodily fluids into bore 121, for example, if device 10 is an implantable device. Those skilled in the art will appreciate that module 12, for example, formed from either silicone or polyurethane, or a combination thereof, may be molded around connector assemblies 120 and includes passages or wire-ways for routing of lead wires from contact assemblies 122 to corresponding feedthrough ports which extend through housing 11; if device 10 is implantable, the feedthrough ports are hermetically sealed. Connector assemblies 120, as a whole, will be discussed in greater detail, below, in conjunction with FIG. 7.

Figure 2:
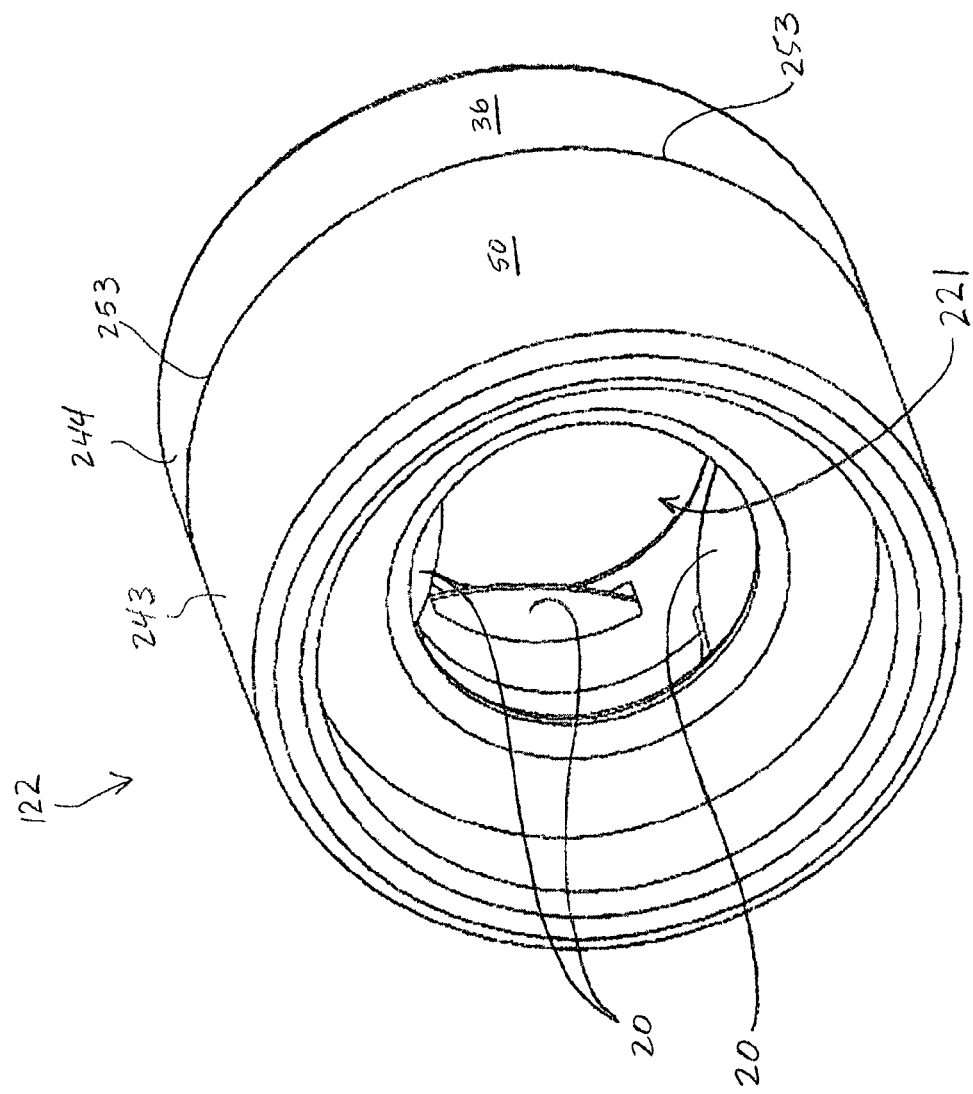
FIG. 2 is a perspective view of a contact assembly, according to some embodiments of the present invention.

FIG. 2 is a perspective view of one of contact assemblies 122, according to some embodiments of the present invention. FIG. 2 illustrates contact assembly 122 including a bore 221, which forms a portion of bore 121 (FIGS. 1A-B), and contact surfaces 20 protruding into bore 221. According to some embodiments, when lead connector 130 is inserted within one of bores 121 formed by connector assemblies 120, such that one of lead connector elements 131 is aligned with contact surfaces 20 within bore 221, surfaces 20 make electrical contact with the aligned connector element 131. FIG. 2 further illustrates contact assembly 122 including two members 243, 244, embodiments of which are described in greater detail in conjunction with FIGS. 3-5; the members are called a cup member 243 and a mounting member 244 in the following description.

Figure 3:
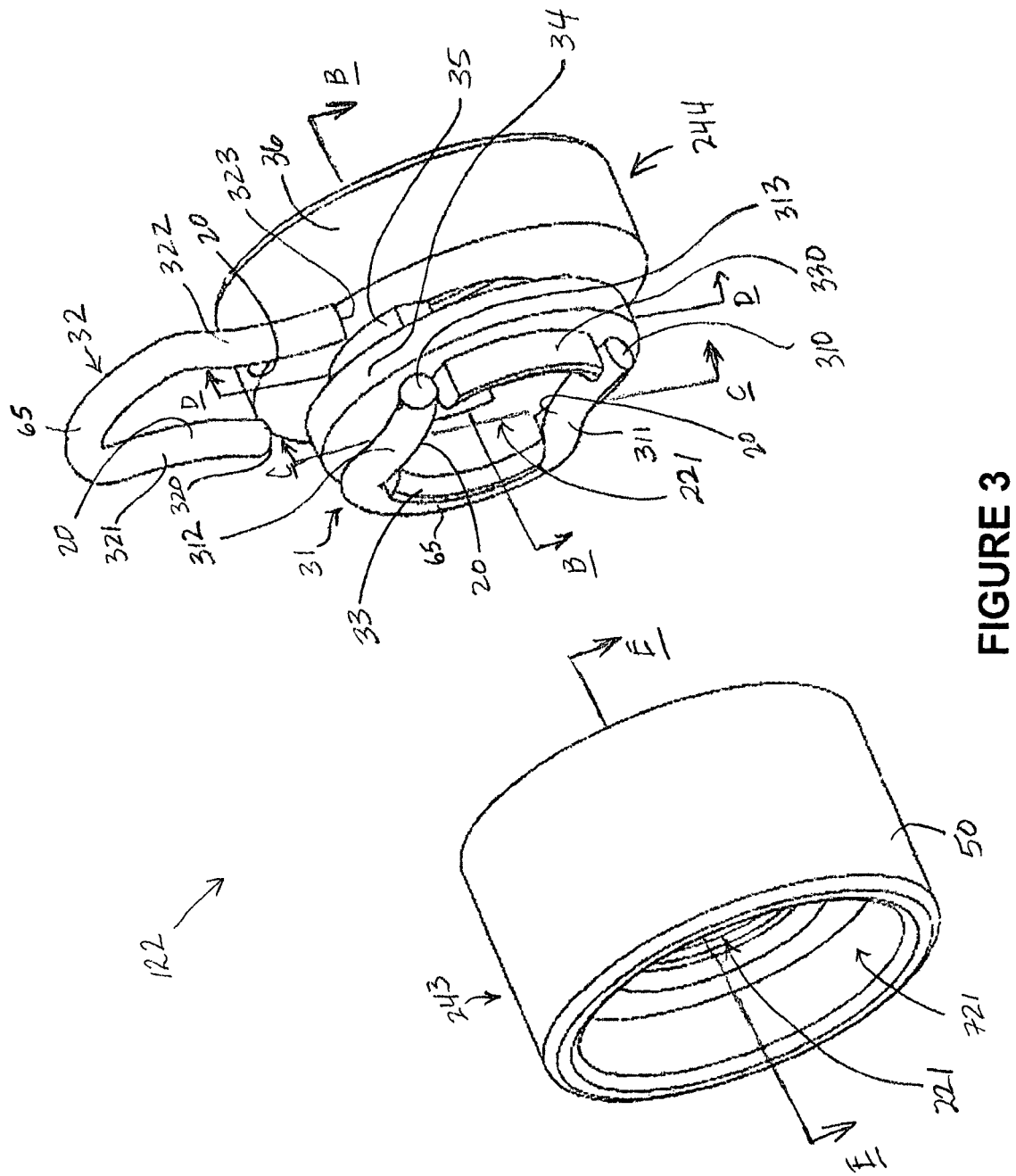
FIG. 3 is an exploded perspective view of the contact assembly of FIG. 2, according to some embodiments of the present invention.
Figure 4C:
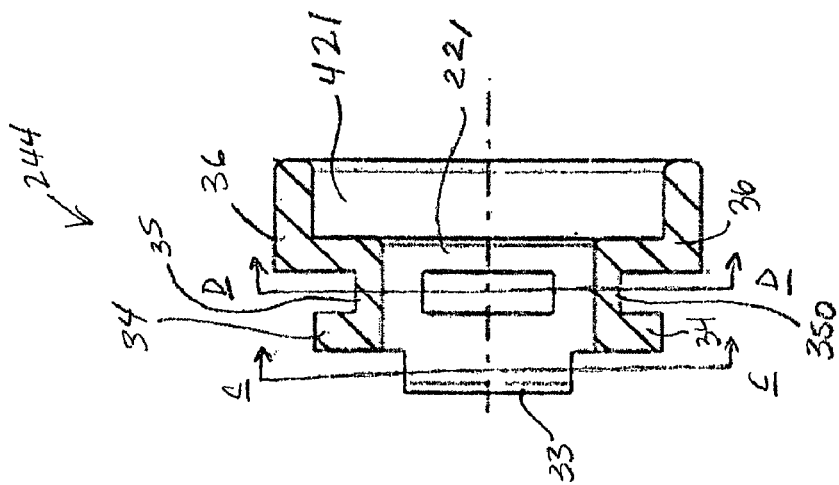
FIGS. 4A-C are cross-sections of a component of the contact assembly shown in FIG. 3, along FIG. 3 section lines C-C, D-D, and B-B, respectively.
Figure 4B:
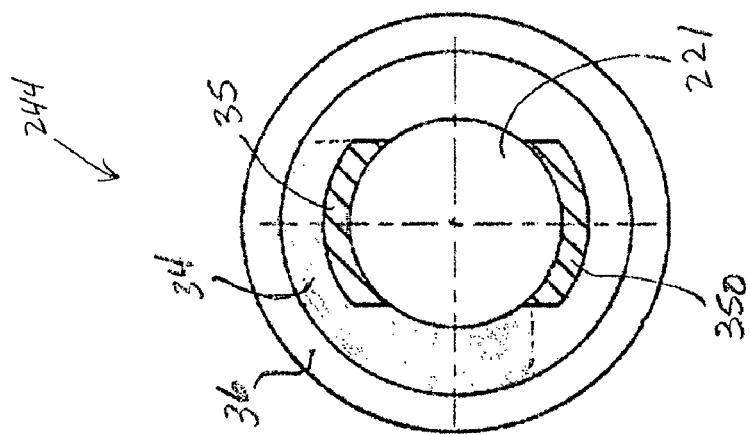
Figure 4A:
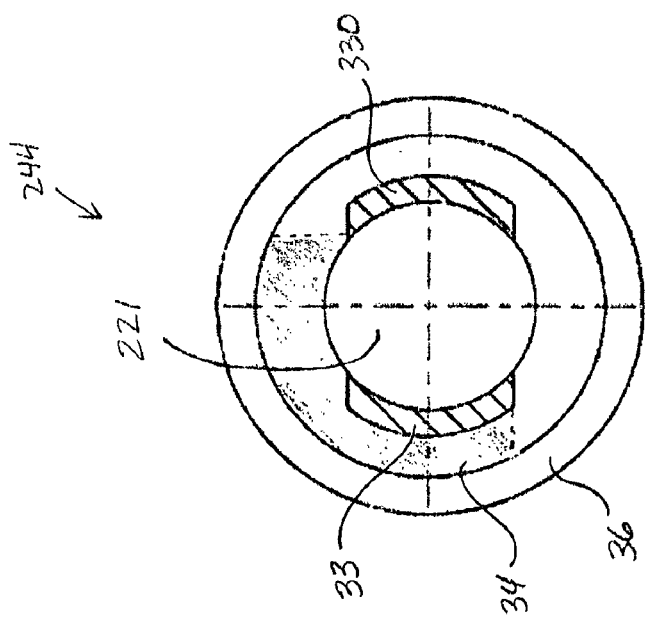

FIG. 3 is an exploded perspective view of contact assembly 122, according to some embodiments of the present invention. FIG. 3 illustrates contact surfaces 20 located along first and second legs 311, 312 of a first contact clip 31 and along first and second legs 321, 322 of a second contact clip 32. According to the illustrated embodiment, a sidewall of mounting member 244, that extends about bore 221, includes first and second mounting sidewalls 33, 35, which each provide for the mounting, or attachment of a corresponding contact clip 31, 32, such that contact surfaces 20 thereof protrude into bore 221. With further reference to FIG. 3, it may be appreciated that each of mounting sidewalls 33, 35 only extend about a portion of a perimeter of bore 221 to allow for legs 311, 312 and 321, 322 to extend into bore 221, and that sidewalls 33, 35 are axially offset from one another, that is, offset from one another along a longitudinal axis of member 244. With reference to FIGS. 4A-B, which are cross-section views of component 244, without clips 31, 32, through lines C-C and D-D of FIG. 3, it may further be appreciated that the portions of the perimeter of bore 221 about which sidewalls 33, 35 extend are offset, about the perimeter, from one another by approximately ninety degrees. It should be noted that although bore 221 has a round cross-section, so that the perimeter thereof defines a circumference of the bore, embodiments of the present invention are not limited to including bores having round cross-sections.

With further reference to FIG. 3, the sidewall of mounting member 244 includes a shoulder 34 located between first and second mounting sidewalls 33, 35; shoulder 34 may stabilize the mounting of first and second contact clips 31, 32 with respect to one another, when clips 31, 32 are attached to mounting sidewalls 33, 35, respectively. Although FIG. 3 illustrates a preferred embodiment in which shoulder 34 extends about an entirety of the perimeter of bore 221, it should be noted that an extent of shoulder 34 can be more limited, according to alternate embodiments, for example, as shown by the shading bounded by dashed lines in FIGS. 4A-B. FIG. 3 further illustrates another shoulder 36 axially offset from shoulder 34 and located alongside second mounting sidewall 35. According to the illustrated embodiment, shoulder 36 extends about the entirety of the perimeter of bore 221 and, with reference to FIG. 4C, which is a cross-section view through section line B-B of FIG. 3, shoulder 36 extends axially away from second mounting sidewall 35 to surround a counter-bore 421 of mounting member 244. Like shoulder 34, as previously described, shoulder 36, according to alternate embodiments, can extend about only a portion of the perimeter of bore 221. Shoulder 36 may serve to further stabilize the mounting of second clip 32, and the extent of shoulder 36 which surrounds counter-bore 421 can interlock with an adjacent member of connector assembly 120, as will be described below in conjunction with FIG. 7.

FIGS. 3 and 4A-C further illustrate a first opposing sidewall 330, opposite first mounting sidewall 33, and a second opposing sidewall 350, opposite second mounting sidewall 35. With particular reference to FIGS. 4A-B, it may be appreciated that first and second opposing sidewalls 330, 350 extend about portions of the perimeter of bore 221 which are offset from the corresponding mounting sidewalls 33, 35 by approximately 180 degrees. According to the illustrated embodiment, first and second opposing sidewalls 330, 350 and first and second mounting sidewalls 33, 35, respectively, are symmetric; such symmetry may be advantageous for ease, or flexibility of assembly, since opposing sidewalls 330, 350 can serve as alternative mounting sidewalls for contact clips 31, 32. According to some embodiments, first and second opposing sidewalls 330, 350 interface with contact clip legs 311, 312 and 321, 322, in proximity to contact clip terminal ends 310, 313 and 320, 323, respectively, in order to pre-load clips 31, 32, respectively. Pre-loading will be described in greater detail, below, in conjunction with FIG. 6.

Figure 5:
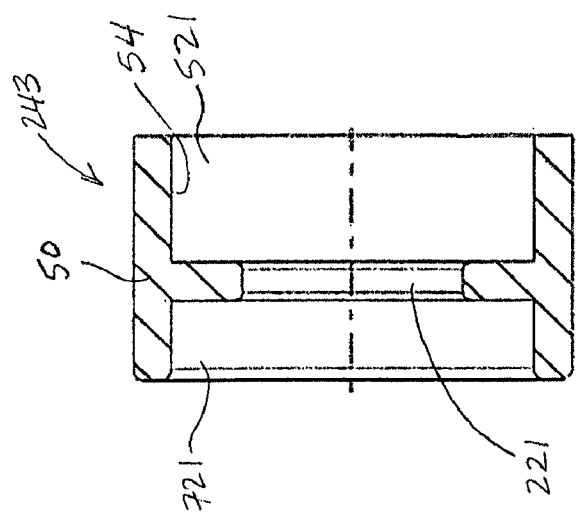
FIG. 5 is a cross-section of another component of the contact assembly shown in FIGS. 2 and 3, along section line E-E of FIG. 3.
Figure 7:
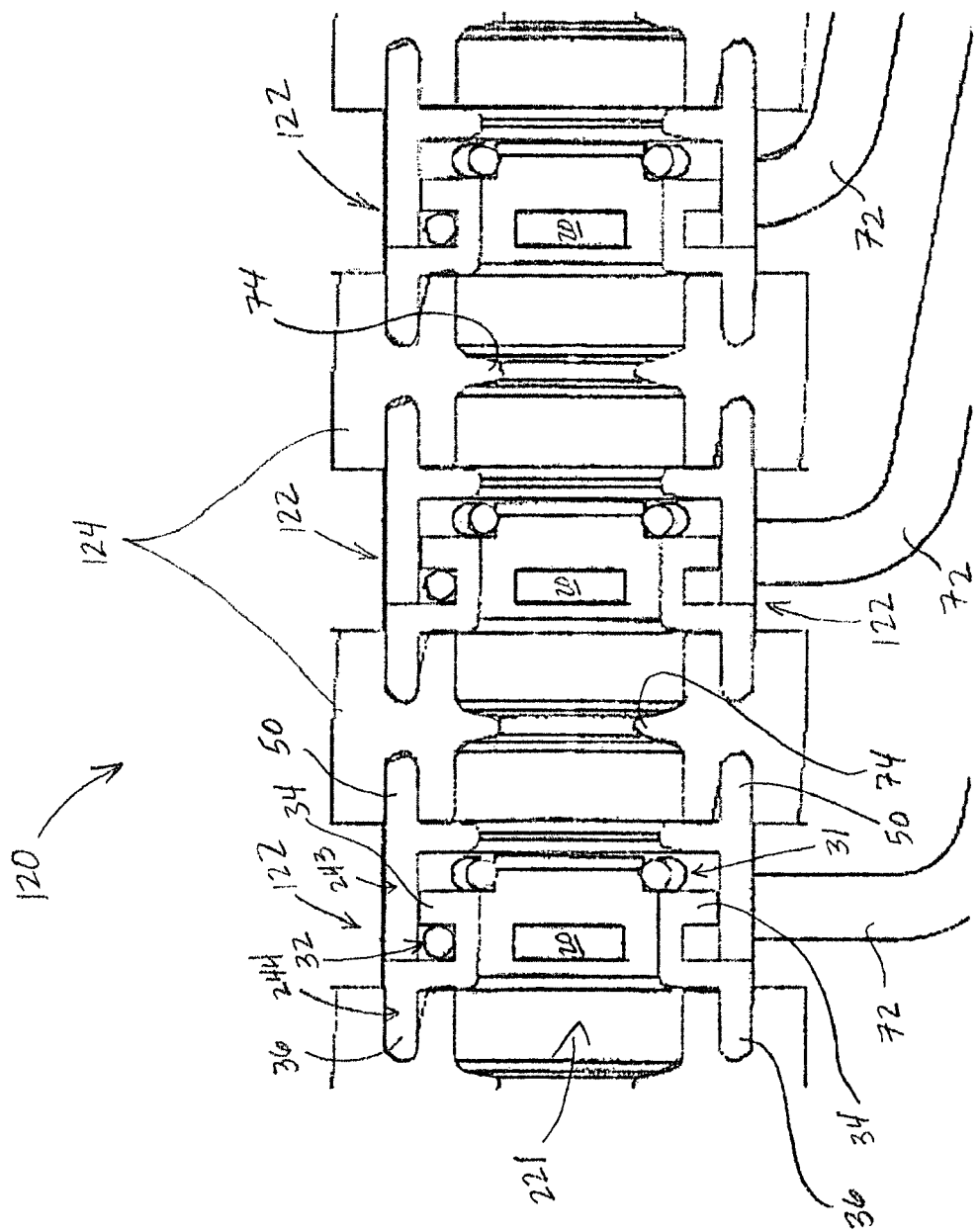
FIG. 7 is a longitudinal cross-section along a portion of the one of the connector assemblies shown in FIG. 1B, according to some embodiments of the present invention.

FIG. 5 is a cross-section view through cup member 243 of contact assembly 122, along section line E-E shown in FIG. 3. FIGS. 3 and 5 illustrate cup member 243 including a sidewall 50 surrounding bore 221 and two counter-bores 521, 721 extending on either side of bore 221. According to the illustrated embodiment, when cup member 243 is assembled together with mounting member 244, that has clips 31, 32 attached thereto, for example, as shown in FIGS. 2 and 7, clips 31, 32 are contained in counter-bore 521, and an inner surface 54 of sidewall 50 surrounding counter-bore 521 fits snugly about shoulder 34 of mounting member 244. The extent of sidewall 50 that surrounds counter-bore 721 can interlock with an adjacent member of connector assembly 120, as will be described below in conjunction with FIG. 7.

Figure 6:
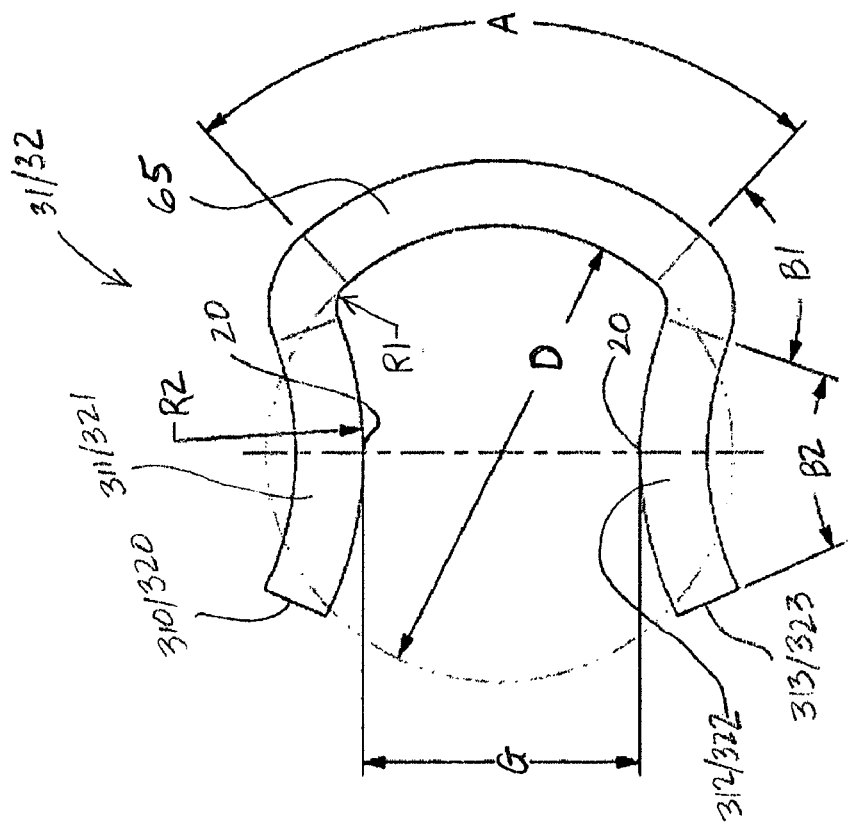
FIG. 6 is a plan view of a contact clip, according to some embodiments of the present invention.

FIG. 6 is a plan view of either of clips 31, 32. FIG. 6 illustrates clip 31/32 including a joining portion 65; joining portion 65 is shown extending between first and second legs 311/321, 312/322, being curved about a circumference of a circle having a diameter D, and spanning a segment of the circle that has a central angle A. FIG. 6 further illustrates each leg 311/321, 312/322 bending inward, toward one another, and then outward away from one another; the inward bending, or curvature, of each leg 311/321, 312/322 extends about a circumference of a circle having a radius R1, and spans a segment of the circle that has a central angle B1, and the outward bending, or curvature, of each extends about a circumference of a circle having a radius R2, and spans a segment of the circle that has a central angle B2. With reference back to FIG. 3, it may be appreciated that joining portion 65 of each clip 31, 32 rests on, and approximately spans the corresponding mounting sidewall 33, 34, that the inward bending of legs 311/321, 312/322 results in the protrusion of contact surfaces 20 into bore 221, and that the outward bending of legs 311/321, 312/322 keeps terminal ends 310/320, 313/323 located outside bore 221, as well as facilitating a rather easy assembly of clips 31/32 onto the sidewall of mounting member 244. According to preferred embodiments of the present invention, clip 31/32 is formed from a wire having a round cross-section, although any cross-sectional geometry may be employed by alternate embodiments.

FIG. 6 further illustrates a relaxed gap G between a peak of the outward bending of leg 311/321 and a peak of the outward bending of leg 312/322. According to the illustrated embodiment, these peaks form opposing contact surfaces 20 and gap G is opened up by insertion of a lead connector, for example, connector 130 (FIG. 1A) therebetween; a spring force of clips 31/32 applies an appropriate contact pressure of contact surfaces 20 against the corresponding connector element 131 positioned within bore 221 of the corresponding contact assembly 122. As mentioned above, opposing sidewalls 330, 350, opposite mounting sidewalls 33, 35, according to some embodiments of the present invention, provide an interface for pre-loading of clips 31, 32. Sidewall 330/350 can pre-load clip 31/32 by spreading opposing legs 311/321, 312/322 further apart from one another and holding a gap between therebetween which is wider than relaxed gap G. Such pre-loading may decrease an axial force required to insert a connector into a connector assembly that includes contact assemblies 122, for example, connector 130 into connector assembly 120.

According to an exemplary embodiment of the present invention, for connector elements, for example, elements 131 of connector 130 (FIG. 1A), which have an outer diameter between approximately 0.044 inch and approximately 0.052 inch, and in which clips 31/32 are not pre-loaded: relaxed gap G is between approximately 0.041 inch and approximately 0.043 inch; diameter D of the circle defining joining portion 65 is between approximately 0.069 inch and approximately 0.071 inch, and central angle A of the segment of the circle defining joining portion 65 is between approximately 82 degrees and approximately 85 degrees; radius R1 of the circle defining the inward bending of legs 311/321, 312/322 is between approximately 0.004 inch and approximately 0.006 inch, and the central angle B1 of the segment of the circle defining the inward bending is between approximately 67 degrees and approximately 70 degrees; and radius R2 of the circle defining the outward bending of legs 311/321, 312/322 is between approximately 0.059 inch and approximately 0.061 inch, and the central angle B2 of the segment of the circle defining the outward bending is between approximately 44 degrees and approximately 46 degrees. An outer diameter of mounting sidewall 33/35, and optionally opposing sidewall 330/350, is between approximately 0.069 inch and approximately 0.071 inch for a line-to-ling fit of clip 31/32 thereon, according to the exemplary embodiment; and an inner diameter of sidewall 33/35 and 330/350 may be approximately 0.056 inch for the exemplary embodiment. Those skilled in the art will understand that these exemplary dimensions may be modified according to various diameters of connector elements 131 and/or if pre-loading is desired.

FIG. 7 is a longitudinal cross-section along a portion of connector assembly 120 (FIG. 1B), according to some embodiments of the present invention. FIG. 7 illustrates a lead wire 72 coupled to each of contact assemblies 122; as previously described, a module, for example, module 12 (FIG. 1A), which contains connector assembly 120, may include wire-ways providing for the routing of each of lead wires 72 to the corresponding feedthrough port. According to an exemplary embodiment of the present invention, each of clips 31, 32, mounting member 244 and cup member 243 are formed from MP35N alloy; alternative conductive materials from which these components may be formed include, without limitation, stainless steel, titanium, tantalum and platinum-iridium. Thus, according to the illustrated embodiment, a fit of cup member 243 over mounting member 244 and clips 31, 32, being mounted thereon, provides intimate contact therebetween for electrical coupling so that lead wires 72, being coupled to cup member 243, power clips 31, 32; alternately, lead wires 72 may be coupled to mounting member 244. With reference back to FIG. 2, in conjunction with FIG. 7, it will be appreciated that an outer diameter of cup member sidewall 50 is approximately equal to an outer diameter of mounting member shoulder 36; as previously described, an inner surface 54 of cup member sidewall 50 (FIG. 5) fits snugly about mounting member shoulder 34, and an interface, or seam 253 between sidewall 50 and shoulder 36 may be laser or resistance spot welded to secure members 243, 244 together.

According to some alternate embodiments, one or both of members 243, 244 are formed from a non-conductive material, for example, a hard plastic or ceramic. If one of members 243, 244 is non-conductive, lead wires 72 may be coupled to the other of members 243, 244, or directly to contact clips 31, 32, in order to power clips 31, 32. If neither of members 243, 244 is conductive, lead wires 72 may be coupled directly to each of clips 31, 32, for example, via a wire-way formed through one of members 243, 244.

FIG. 7 further illustrates seal members 124 including internally-projecting sealing rings 74, for mating with insulative spacers disposed between connector elements 131 of connector 130 (FIG. 1A), and an interlocking of each seal member 124 with adjacent contact assemblies 120. As previously described, mounting member shoulder 36 extends to provide for the interlocking, as does cup member sidewall 50. The illustrated interlocking features of connector assembly 120 are described in greater detail in commonly-assigned U.S. Pat. No. 6,895,276, salient portions of which are hereby incorporated by reference.

In the foregoing detailed description, the invention has been described with reference to specific embodiments. However, it may be appreciated that various modifications and changes can be made without departing from the scope of the invention as set forth in the appended claims. For example, although embodiments of a contact assembly presented herein include a pair of contact clips, for example, clips 31, 32, to make common electrical contact with a single lead connector element, for example, one of elements 131, each clip of the pair of contact clips may be isolated from one another within the contact assembly, for example, via mounting member 244 being formed from a non-conductive material, and individually coupled to independent lead wires for electrical coupling of two independent lead connector elements having been inserted within the contact assembly.

The invention claimed is:

1. A method for assembling a connector assembly for a connector module of a medical device, the connector assembly including at least one contact assembly, each of the at least one contact assembly including a mounting member, a first contact clip and a second contact clip, the mounting member including a bore, to receive axial insertion of a medical electrical lead connector therein, a first pair of opposing mounting sidewalls extending about the bore, and a second pair of opposing mounting sidewalls, axially offset from the first pair of opposing mounting sidewalls and extending about the bore, each of the first and second contact clips including a joining portion and a pair of opposing curved legs extending from the joining portion, and the method comprising:

mounting the first contact clip to one of the first pair of opposing mounting sidewalls of the mounting member, so that an inward bending portion of each of the opposing curved legs of the first contact clip bends into and out from the bore, and the joining portion of the first contact clip rests on the one of the first pair of opposing mounting sidewalls, being positioned on a first side of a shoulder of the mounting member, the shoulder being axially offset from the first pair of opposing sidewalls; and mounting the second contact clip to one of the second pair of opposing mounting sidewalls of the mounting member, so that an inward bending portion of each of the opposing curved legs of the second contact clip bends into and out from the bore, and the joining portion of the second contact clip rests on the one of the second pair of opposing sidewalls, being positioned on a second side of the shoulder, the second side being opposite the first side.

2. The method of claim 1, wherein mounting the first contact clip comprises moving, in a first direction, the opposing curved legs of the first contact clip past the one of the first pair of opposing mounting sidewalls and toward the other of the first pair of opposing mounting sidewalls.

3. The method of claim 2, wherein mounting the second contact clip comprises moving, in a second direction, the opposing curved legs of the second contact clip past the one of the second pair of opposing mounting sidewalls and toward the other of the second pair of opposing mounting sidewalls, the second direction being approximately orthogonal to the first direction.

4. The method of claim 1, wherein:
   mounting the first contact clip results in an outward bending portion of each curved leg of the first contact clip interfacing with the other of the first pair of opposing mounting sidewalls; and
   mounting the second contact clip results in an outward bending portion of each curved leg of the second contact clip interfacing with the other of the second pair of opposing mounting sidewalls.

5. The method of claim 1, further comprising fitting a cup member around the mounting member of each of the at least one contact assemblies, such that a sidewall of the cup member contains the mounted first and second contact clips.

6. The method of claim 5, wherein fitting the cup member comprises moving the cup member in a direction approximately parallel to a longitudinal axis of the mounting member.

7. The method of claim 5, further comprising welding the cup member to the mounting member at an interface between the sidewall of the cup member and another shoulder of the mounting member.

8. The method of claim 5, wherein fitting the cup member results in a snug fit of the sidewall of the cup member about the shoulder of the mounting member.

9. The method of claim 5, wherein fitting the cup member results in intimate contact between the cup member and the mounted first and second contact clips.

10. The method of claim 5, further comprising electrically coupling a lead wire to the cup member.

11. The method of claim 5, wherein the at least one contact assembly includes a first contact assembly and a second contact assembly, and further comprising joining the first contact assembly to the second contact assembly by interlocking a first side of a seal member with a portion of the mounting member of one of the first and second contact assemblies and interlocking a second side of the seal member with a portion of the cup member of the other of the first and second contact assemblies.

12. The method of claim 1, further comprising electrically coupling a lead wire to the mounting member.

13. The method of claim 1, further comprising interlocking a seal member with a portion of the mounting member of the at least one contact assembly.

* * * * *